(12) United States Patent
Avery et al.

(10) Patent No.: US 7,465,439 B2
(45) Date of Patent: Dec. 16, 2008

(54) HOME AND PERSONAL CARE COMPOSITIONS COMPRISING SILICON-BASED LUBRICANTS

(75) Inventors: Andrew Richard Avery, Wirral (GB); Dominique Charmot, Campbell, CA (US); Jean M Frechet, Oakland, CA (US); Damian Hajduk, San Jose, CA (US); Ezat Khoshdel, Wirral (GB); Mingjun Liu, Santa Clara, CA (US)

(73) Assignee: Conopco, Inc., Englewood Cliffs, NJ (US)

( * ) Notice: Subject to any disclaimer, the term of this patent is extended or adjusted under 35 U.S.C. 154(b) by 276 days.

(21) Appl. No.: 10/542,421

(22) PCT Filed: Dec. 29, 2003

(86) PCT No.: PCT/EP03/14995

§ 371 (c)(1),
(2), (4) Date: Dec. 12, 2005

(87) PCT Pub. No.: WO2004/162634

PCT Pub. Date: Jul. 29, 2004

(65) Prior Publication Data

US 2006/0100126 A1    May 11, 2006

(30) Foreign Application Priority Data

Jan. 14, 2003    (GB)    ................ 0300808.3

(51) Int. Cl.
*A61Q 5/00*    (2006.01)
*C08G 77/44*    (2006.01)

(52) U.S. Cl. .................... 424/70.12; 524/837; 525/477; 525/478; 528/31; 528/32

(58) Field of Classification Search ....................... None
See application file for complete search history.

(56) References Cited

U.S. PATENT DOCUMENTS

| | | | |
|---|---|---|---|
| 5,654,362 A | 8/1997 | Schulz, Jr. et al. | 524/862 |
| 6,150,488 A * | 11/2000 | Martin | 528/34 |
| 6,488,918 B2 | 12/2002 | Hess et al. | 424/62 |
| 2002/0131947 A1 * | 9/2002 | Nakanishi | 424/70.12 |

FOREIGN PATENT DOCUMENTS

| | | |
|---|---|---|
| EP | 0 934 959 | 8/1999 |
| EP | 1 101 487 | 5/2002 |
| EP | 1 213 009 | 6/2002 |
| EP | 1 219 289 | 7/2002 |
| EP | 582 152 | 4/2003 |
| JP | 2001 253811 | 9/2001 |
| WO | 1 010 715 | 6/2000 |
| WO | 01/30886 | 5/2001 |
| WO | 1 132 430 | 9/2001 |
| WO | 03/049711 | 6/2003 |

* cited by examiner

*Primary Examiner*—Marc S Zimmer
(74) *Attorney, Agent, or Firm*—Karen E. Klumas

(57) ABSTRACT

A composition for personal, home, or laundry treatment comprising a polymer made up of one or more crosslinked rake or comb silicone copolymer segments. A process for making copolymers for use in such compositions involves hydrosilylation in the presence of a catalyst.

17 Claims, No Drawings

HOME AND PERSONAL CARE COMPOSITIONS COMPRISING SILICON-BASED LUBRICANTS

TECHNICAL FIELD

The invention is concerned with home and personal care compositions that comprise novel, silicone-based hydrophobic oils, waxes and gums. It is particularly concerned with hair treatment compositions comprising such novel materials, and with processes for preparing the novel materials. The oils, waxes or gums are polymers which comprise one or more copolymer segments with a silicone-based backbone and a plurality of silicone side groups, also called comb or rake copolymer segments.

BACKGROUND AND PRIOR ART

Home and personal care compositions include products such as hair shampoos, hair conditioners, hair styling products, shower gels, fabric washing powders and liquids, fabric softeners, laundry dryer aids, easy-iron sprays, deodorant sticks, waxes and polishes (such as car and furniture waxes), cleaning sprays, abrasive cleaners, carpet cleaners, makeup, lipstick, eye shadow, skin creams, massage oils, lotions, ointments, sunscreens, shaving products, depilatory products, hair colorants, toothpastes, paints, varnishes and lacquers (such as brickwork sealants). Frequently, there is a need for hydrophobic oils waxes or gums to be present in such products in order to provide desirable attributes to the product such as feel on the skin, smooth hair, soft fabric feel, water repellency, dirt repellency, ease of spread, shine.

Silicone-based hydrophobic oils, waxes and gums are often used in such home and personal care compositions. Silicone-based hydrophobic oils can have advantages over organic oils for lubrication and shine.

In spite of these advantages, silicone materials tend to be incorporated into products at relatively low levels. This may be because these ingredients are generally expensive compared to other components, so increase the cost of products. Also, levels of incorporation are limited by the mutual compatibility of silicones with the other components, which can lead to instability and separation of the silicone into a separate layer on storage of the product. This is undesirable as it looks unattractive to the consumer and also because it can lead to uneven dosing of the components. Also, high levels of silicones in products can lead to an undesirable build-up of silicones on the hair, leading to some consumers feeling that the hair is dirty or greasy Special emulsifiers may also be needed to disperse silicone hydrophobes in products.

In order to prepare stable products with a balance of attributes that are attractive to the consumer, the formulation developer is faced with the challenge of ensuring the compatibility of the hydrophobic material with the other ingredients in the composition. There is also the problem of achieving the desired effects with relatively low levels of silicone in the composition.

In particular, for compositions which are aimed at improving the combability and smoothness of wet and/or of dry hair there is a need for silicones which provide high levels of lubricity when present at low levels in compositions. This is also the case for fabric softening products and other products where the role of the silicone hydrophobe is to provide lubrication.

Hence there is a need for alternative silicones to complement the current range of available silicone-based hydrophobes. Moreover there is also a need for silicones which can provide higher levels of lubricity than current materials when used in home and personal care compositions.

The conventional ingredients in home and personal care compositions are generally organic in nature, by which is meant based on carbon chemistry. The essential incompatibility between silicone and organic molecules has led to the development of silicone polymeric materials with organic substituent groups, with the expectation that such silicone polymers will be more compatible with other ingredients in products (such as for making stable emulsions) and with the organic substrates upon which the product is used (such as hair and skin and fabrics).

EP 0 582 152 discloses a graft copolymer or alternating block copolymer linked by a sulfide linkage.

Surprisingly, it has now been found that new hydrophobic polymeric silicones, where the silicone backbone of the polymer is furnished with silicone substituent groups in order to form comb or rake shaped molecules, are suitable for use in home and personal care products as hydrophobic oils, waxes and gums. It has also been found that the new hydrophobic polymeric silicones can be more effective than known silicones as lubricants. This is particularly the case for home and personal care compositions, and more particularly in hair conditioning compositions.

SUMMARY OF THE INVENTION

In a first aspect, the invention is concerned with a composition for personal, home, or laundry treatment comprising a polymer which comprises a copolymer segment, the copolymer segment comprising monomeric units according to formula A:

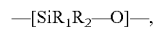

and monomeric units according to formula B:

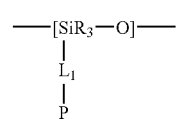

and end groups, wherein $L_1$ is an organic linking group and P is a polymer or oligomer comprising 2 or more monomeric units G;

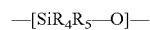

and P further comprises an end group, wherein $R_1$, $R_2$, $R_3$, $R_4$ and $R_5$ are independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, and combinations thereof.

DETAILED DESCRIPTION AND PREFERRED EMBODIMENTS OF THE INVENTION

The term "alkyl" is used herein to refer to a branched or unbranched, saturated or unsaturated acyclic hydrocarbon radical. Suitable alkyl radicals include, for example, methyl, ethyl, n-propyl, isopropyl, propenyl (or allyl), hexyl, vinyl, n-butyl, tert-butyl, iso-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom to any carbon of the alkyl is replaced by another group such as a halogen, aryl, substituted aryl, cycloalkyl, substituted cycloalkyl, and combinations thereof. Suitable substituted alkyls include, for example, benzyl, trifluoromethyl and the like.

The term "heteroalkyl" refers to an alkyl as described above in which one or more carbon atoms of the alkyl is replaced by a heteroatom selected from the group consisting of N, O, P, B, S, Si, Se and Ge. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl, $Me_3SiOCH_2(CH_3)_2C$— and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept-4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorus, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl, and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholine, and the like.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphino, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone. Specific examples of substituted aryls include perfluorophenyl, chlorophenyl, 3,5-dimethylphenyl, 2,6-diisopropylphenyl and the like.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more nonaromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Substituted heteroaryl" refers to heteroaryl as just described including in which one or more hydrogen atoms to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the —$OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the —$SiZ^1Z^2Z^3$ radical, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the —$BZ^1Z^2$ group, where each of $Z^1$ and $Z^2$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group —$PZ^1_n$, where each of $Z^1$ is independently selected from the group consisting of hydrogen oxygen, substituted or unsubstituted alkyl, cycloalkyl, heterocycloalkyl, heterocyclic, aryl, heteroaryl, silyl, alkoxy, aryloxy, amino and combinations thereof, and where n is 0 to 4 depending on the phosphorus oxidation state.

The term "amino" is used herein to refer to the group —$NZ^1Z^2$, where each of $Z^1$ and $Z^2$ is independently selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

As used herein, "copolymer" refers to a polymer comprising at least two differing monomer compositions. A "block copolymer" refers to a copolymer where the monomers are not incorporated into the polymer architecture in a solely statistical or uncontrolled manner. A "random copolymer" referes to a copolymer where the monomers are incorporated into the polymer architecture in a solely statistical or uncontrolled manner.

A "block" within the scope of the block copolymers of this invention typically comprises about 5 or more monomers of a single type (with the random blocks being defined by composition and/or weight percent, as described above). In particular embodiments, the number of monomers within a single block may be about 10 or more, about 15 or more, about 20 or more or about 50 or more. Each block may have a desired architecture and thus, each block may be linear.

Polymer

It is preferred if the polymer is water-insoluble by which it is meant that the solubility of the polymer in water at 25° C. is 1% by weight of water or less, more preferably 0.5% by weight of water or less, most preferably 0.1% by weight of water or less, and even more preferably, 0.05% by weight of water or less. It is also preferred if the polymer is non-volatile, by which it is meant that the polymer has a vapour pressure at 25° C. of 10 Pa or less, more preferably 1 Pa or less, and even more preferably 0.5 Pa or less The preferred level of polymer in compositions according to the invention is dependent upon the nature of the home or personal care product. For products such as hair oils or massage oils the composition may comprise up to 99% by weight of the polymer, preferably up to 50% by weight, more preferably up to 30% by weight. For products which are water-based such as shampoos, shower gels or hair conditioners, a suitable level of polymer is from 0.1 to 10%, preferably 0.2 to 6%, more preferably from 0.2 to 4% by weight of the total composition.

Compositions according to the invention will suitably be water-based, meaning that they will preferably comprise 40% or more, preferably 50% or more, more preferably 70% or more by weight of water.

For certain applications, the compositions may be based on a different solvent, such as ethanol.

For products such as polishes, levels of polymer from 0.01% to 5% may be sufficient to give the desired effect.

When the polymer is employed in water-based compositions, the composition will further comprise an aqueous carrier solution. Suitably this comprise water and surfactant. For cosmetic and personal care compositions, a cosmetically acceptable aqueous carrier solution will be necessary.

The polymer may be present as a separate phase in water-based composition, either as a separate layer or dispersed into the composition in the form of an emulsion. The polymer may be present as the discontinuous or as the continuous phase of the emulsion. A suitable emulsifying surfactant may be employed to lend physical stability to the emulsion.

Graft copolymers or alternating block copolymers linked by a sulfide linkage as disclosed in EP0 582 152 are not considered as polymers according to the invention.

Suitably, the groups $R_1$, $R_2$, $R_3$, $R_4$ and $R_5$ each independently have from 1 to 40 carbon atoms, preferably from 1 to 10 carbon atoms, more preferably up to 6 carbon atoms. It is preferred if $R_1$, $R_2$, $R_3$, $R_4$ and $R_5$ are all the same. In particular, it is preferred if $R_1$, $R_2$, $R_3$, $R_4$ and $R_5$ are selected from alkyl groups with up to 4 carbon atoms, phenyl groups, and mixtures thereof. More preferably all are ethyl or methyl groups.

Although the polymer may comprise monomeric units other than those according to formulae A, B and G. it is preferred if more than 70% by weight of the polymer is comprised of said units, more preferably more than 80% by weight, most preferably more than 90% by weight.

It is particularly preferred if the polymer consists essentially of monomeric units according to formulae A, B and G in combination with end groups and optionally crosslinking units.

However, when the polymer comprises other monomeric units than those according to formulae A, B and G, it is preferred if those other monomeric units are amino-functionalised organosiloxane units. This is particularly preferred when the composition is a hair treatment composition. It is particularly preferred if such amino-functionalised units are present as part of the polymer segment P.

The end groups of the copolymer segment are present to terminate the polymer chains. Suitable end groups are as follows:

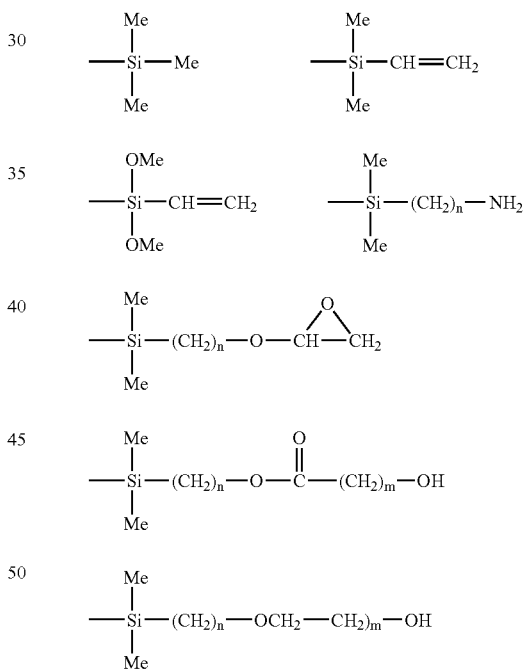

In the above formulae, Me represents a methyl group ($CH_3$). The end group is linked to the rest of the molecule either directly or through an oxygen linking atom. The values of m and n in the formulae for the end groups are suitably independently chosen from 1 to 12, preferably from 1 to 6, more preferably from 1 to 4. A preferred end group is silicon linked to three methyl groups, —Si($CH_3$)$_3$.

The copolymer segment comprises monomeric units according to formula A:

—[SiR$_1$R$_2$—O]—,  A)

and monomeric units according to formula B:

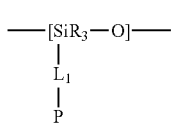

B)

The linking group $L_1$ of formula B is an organic linking group, by which it is meant that the linking group comprises one or more carbon atoms. Preferably, the linking group comprises the grouping —$CH_2$—$(CH_2)_n$— wherein n is from 1 to 8, more preferably from 1 to 4, most preferably 1 or 2. It is also preferred if the linking group is of the form —$CH_2$—$(CH_2)_n$-$L_2$-, in other words that the group further comprises a second linking group $L_2$, wherein $L_2$ is selected from the group consisting of ether, amino, amide, carbonate, urea and ester linkages.

Suitably, $L_2$ can be

—O—$(CH_2)_s$—,   1)

—O—CO—$(CH_2)_s$—,   2)

—NH—CO—$(CH_2)_s$—,   3)

—CO—O—$(CH_2)_s$—,   4)

—CO—NH—$(CH_2)_s$—,   5)

—OCO—O—$(CH_2)_s$—   6)

—ONH—CO—$(CH_2)_s$—   7)

—CONH—CO—$(CH_2)_s$—   8)

wherein s is from 1 to 18, preferably 1 to 18, more preferably 1 to 4.

It has also been found that it is preferable if the polymer for use in the invention comprises 2 or more crosslinked copolymer segments. By this it is meant that the polymer comprises two or more copolymer segments which are interconnected, not at their ends, but instead by a cross linking unit which connects two monomeric units in the respective comb or rake sections. It is preferred if the crosslinking unit connecting the copolymer segments comprises a polyorganosiloxane segment. Suitable crosslinking units are known to those skilled in the art of polymer chemistry.

The one or more copolymer segments of the polymers for use in compositions according to the invention each comprise, and preferably consist essentially of, by number an average of p monomeric units according to formula A and q monomeric units according to formula B, while P comprises an average of r monomeric units according to formula G. It is preferred if p is from 40 to 15 000, q is from 5 to 1000 and r is from 10 to 500. More preferably p is from 150 to 10 000, most preferably from 500 to 1 500. More preferably q is from 15 to 500, most preferably from 50 to 100. More preferably r is from 20 to 500, most preferably from 50 to 300.

The polymer suitable for the invention may comprise only one copolymer segment, but it is preferred if it comprises 2 or more crosslinked copolymer segments, more preferably 2 to 30, even more preferably 3 to 20, most preferably 5 to 15. It is thought that this preferred crosslinking enhances the lubricity of the polymer.

The number of crosslinked copolymer segments is derivable from the measured molecular weight of the polymer in relation to the values of p, q and r used for the starting materials.

The polymers according to the invention are particularly useful as conditioning agents and lubricants in hair treatment compositions.

For hair treatment compositions, it is preferred if the one or more copolymer segments of the polymer have average values of p, q and r such that p is from 700 to 900, q is from 40 to 60 and r is from 60 to 75. It is also preferred if $R_1$, $R_2$, $R_3$, $R_4$ and $R_5$ are methyl groups, and it is further preferred if $L_1$ is $(CH_2)_g$COO and g is an integer from 2 to 10, preferably from 3 to 6, most preferably 4. Preferably, the polymer consists essentially of 2 or more crosslinked copolymer segments more preferably 5 to 15. A preferred crosslinking agent is one which comprises a polydimethylsiloxane polymer segment P as described above.

A preferred route for the preparation or manufacture of the polymer for use in compositions according to the invention is by means of hydrosilylation chemistry. The term hydrosilylation refers to the addition of Si—H bonds to organic double bonds (olefins) such as C=C as shown below in scheme 1:

Scheme 1

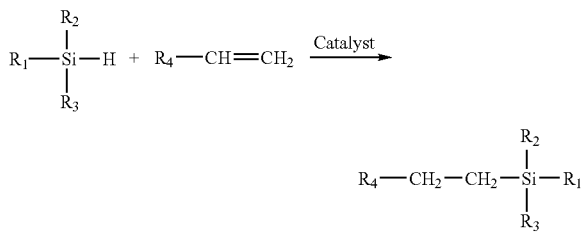

Hydrosilylation is one of the basic methods for the synthesis of organosilicone compounds and organic silyl derivatives, particularly the formation of silicone networks. No by-products are formed by this reaction, and the addition to the olefin can be Markownikoff or anti-Markownikoff depending upon the nature of the olefin.

In Scheme 1 the groups not shown in the reaction are not intended to represent methyl groups. They can be any moiety capable of the bonding represented in the scheme. They are unimportant for purposes of discussing the hydrosilylation reaction scheme.

Suitable catalysts for the hydrosilylation reaction are periodic group 8-10 (VIII) metal complexes or supported metal catalysts. Platinum and compounds thereof are preferred catalysts. Soluble platinum olefin catalysts are particularly preferred. A suitable concentration of catalyst is 1 to 2 parts per million of the reaction mixture.

Rhodium (I) complexes are also preferred catalysts.

Hence a preferred process for obtaining the polymer for use in compositions according to the invention comprises the steps of:

i) forming a copolymer segment precursor comprising monomeric units according to formula A:

   A) and monomeric precursor units according to formula X:

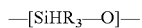   X)

ii) reacting the copolymer backbone precursor with a compound according to formula Y;

$$CH_2=CH-L_3-P \qquad \qquad Y)$$

in a hydrosilylation reaction in the presence of a suitable catalyst,
wherein $L_3$ is an organic group which may be absent and wherein the quantity of Y is such that the monomeric precursor units X are substantially converted to the monomeric units B of the polymer for use in the invention. P is a polyorganosiloxane group.

Hence the group $-CH_2-CH_2-L_3-P$ formed by the hydrosilylation reaction between Y and the SiH part of the monomeric unit X corresponds to the group $-L_1-P$ of the monomeric unit B of polymers for use in compositions according to the invention.

It is preferred if a small quantity of crosslinking agent is present when the reaction is carried out whereby the resulting polymer is made up of two or more crosslinked copolymer segments. A suitable level of crosslinking agent in the reaction mixture is 0.01 to 20% by weight of reaction mixture, preferably 0.05 to 10%, more preferably 0.1 to 5%. A preferred crosslinking agent comprises a polyorganosiloxane segment. It is particularly preferred if the crosslinking agent is according to the formula:

$$CH_2=CH-L_3-P-L_4-CH=CH_2$$

where $L_4$ is an optional organic linking group. Preferably $L_4$ and $L_3$ are the same. Both may be absent. In a particularly preferred process, the crosslinking agent is provided as an impurity present in the commercial raw material used to supply compound Y for the reaction.

The process of Scheme 1 may be carried out in bulk, in solution or preferably by an emulsion polymerisation route.

In one embodiment, a preformed copolymeric backbone may be combined with side chain or graft polymers in the presence of a catalyst. One example of a preformed backbone polymer is poly(dimethylsiloxane-co-methylhydrosiloxane), which is commercially available in several different molecular weights and compositions. In one embodiment, the side chains may be vinyl-terminated polydimethylsiloxanes, which may be prepared by the reaction of hydroxyl-terminated polydimethylsiloxanes and 4-pentenoyl chloride in the presence of triethylamine. The side chains and backbone are then combined with a suitable catalyst, such as platinum, and reacted at an appropriate temperature for an appropriate time.

In a preferred process, the reaction mixture is maintained at a temperature from 40 to 80° C., preferably from 45 to 60° C., for a time greater than 30 minutes, preferably greater than 90 minutes, more preferably greater than 90 minutes.

One advantage of the processes described above is that the molecular weight of the backbone and graft polymers are known. One factor that is not controlled with this method is that the distance between grafting sites on the backbone. Also, there may be circumstances where preformed backbones with desired characteristics, such as molecular weight, are not commercially available.

A specific example of the above described grafting route is shown below in Scheme 2:

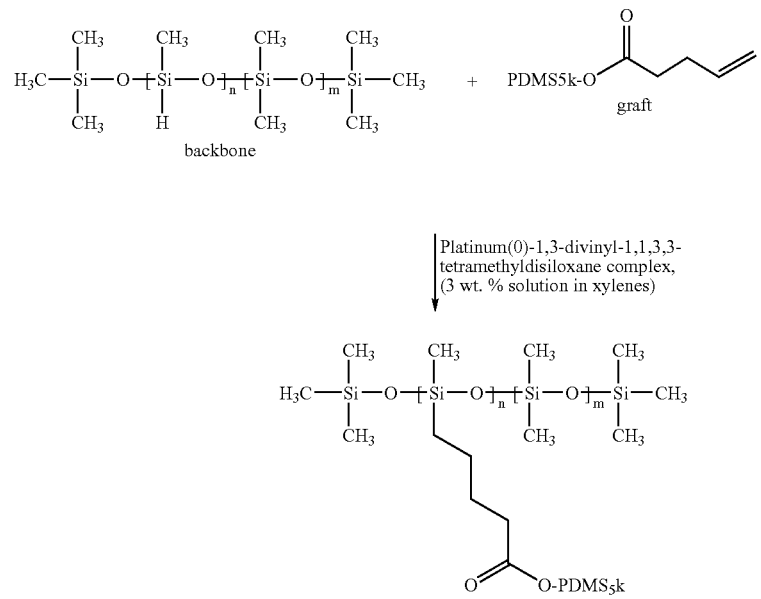

In Scheme 2 PDMS5k represents a polydimethylsiloxane segment having a molecular weight of 5,000 unified atomic mass units and n and m are greater than one.

An alternative method exists for making polymers suitable for the present invention, which allows for control of the graft spacing on the backbone as well as control of the graft molecular weight. This method may also result in higher molecular weight copolymers.

This method can be generally characterized by the reaction as shown below in scheme 3:

Scheme 3

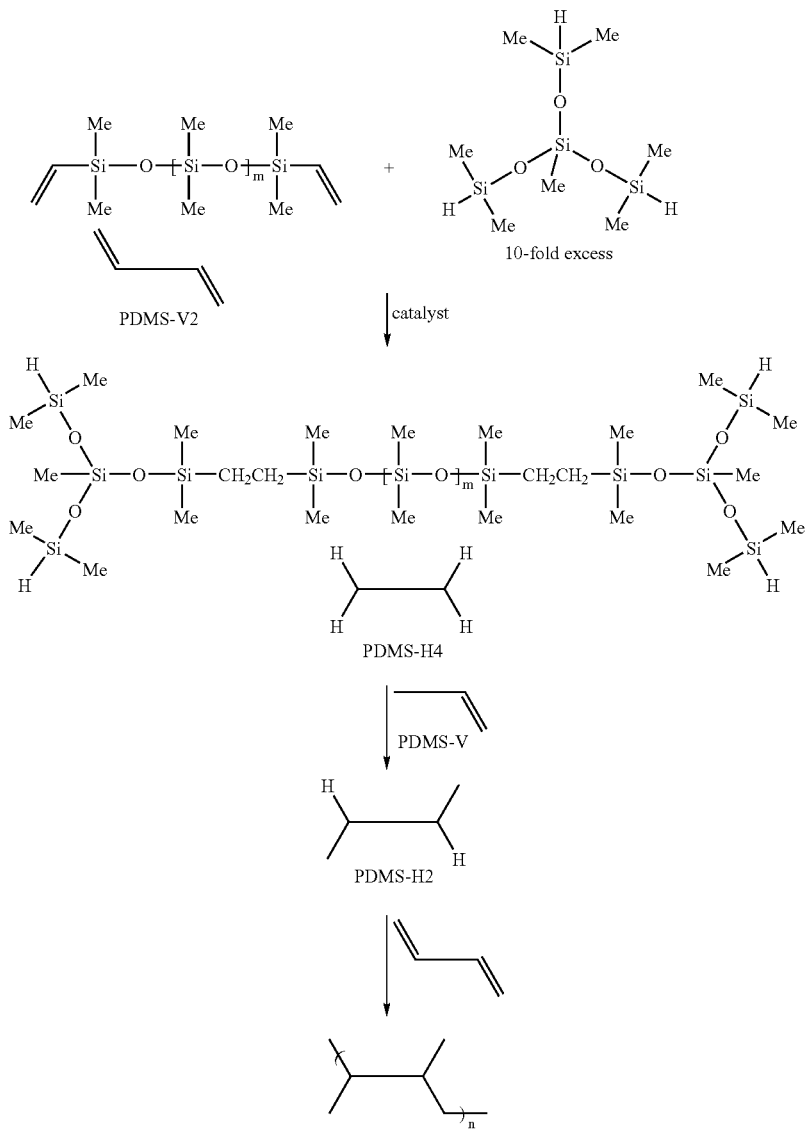

In Scheme 3, PDMS—V2 is a divinyl-terminated polydimethylsiloxane; PDMS—V is a monovinyl-terminated polydimethylsiloxane (which can be the compound according to formula Y); PDMS—H4 is a PDMS segment having four reactive H groups, PDMS—H2 is a PDMS segment having 2 reactive H groups, m is greater than 1, and n is one or more.

PDMS—V2 is available in a variety of molecular weights. Some commercially available materials include PDMS—V2 polymers having molecular weights of 6,000, 17,000 and 28,000 Da. Also, monovinyl-terminated PDMS is available in a variety of molecular weights. Some examples include weights of 1,000, 5,000 and 10,000 unified atomic mass units.

In Scheme 3, PDMS—V2 is reacted with an excess of the siloxane molecule shown above. The siloxane molecules react with the vinyl end groups of PDMS—V2, creating a polydimethylsiloxane polymer having the structure PDMS—H4. This polymer is then reacted with monovinyl-terminated PDMS (PDMS—V), which is used in an amount equal to 0.5 PDMS—V molecules per available Si—H group of PDMS—H4. This results in the structure shown as PDMS—H2. This polymer is then further reacted with PDMS—V2, which reacts at the available Si—H sites of PDMS—H2. The resulting polymer has evenly spaced grafts along the backbone.

The ratio of PDMS—V2 to PDMS—H2 can be from 0.5:1 to 1:0.5. Preferably, the ratio is from 0.9:1 to 1:1.1.

Generally, the polymerization proceeds under polymerization conditions. Polymerization conditions include the ratios of starting materials, temperature, pressure, atmosphere and reaction time. The polymerization conditions that may be used include: Temperatures for polymerization are typically in the range of from about 20° C. to about 100° C., more specifically in the range of from about 25° C. to about 80° C. and even more specifically in the range of from about 30° C. to about 60° C. The atmosphere may be controlled, with an inert atmosphere being preferred, such as nitrogen or argon. The polymerization may be carried out in bulk. Polymerization reaction time may be in the range of from about 0.5 hours to about 72 hours, specifically from about 1 hour to about 24 hours and more specifically from about 2 hours to about 12 hours.

Hair Treatment Compositions

Hair treatment compositions according to the invention may suitably take the form of shampoos, conditioners, sprays, mousses, oils, styling products, hair colouring products or lotions. Preferred hair treatment composition forms are shampoos, conditioners and mousses.

Shampoo Compositions

Shampoo compositions according to the invention will comprise one or more cleansing surfactants which are cosmetically acceptable and suitable for topical application to the hair.

Suitable cleansing surfactants, which may be used singularly or in combination, are selected from anionic, nonionic, amphoteric and zwitterionic surfactants, and mixtures thereof.

Anionic Cleansing Surfactant

Shampoo compositions according to the invention will typically comprise one or more anionic cleansing surfactants which are cosmetically acceptable and suitable for topical application to the hair.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3).

Mixtures of any of the foregoing anionic cleansing surfactants may also be suitable.

The total amount of anionic cleansing surfactant in shampoo compositions of the invention is generally from 5 to 30, preferably from 6 to 20, more preferably from 8 to 16 percent by weight of the composition.

Co-surfactant

Shampoo compositions according to the invention can optionally include co-surfactants, to help impart aesthetic, physical or cleansing properties to the composition.

A preferred example is an amphoteric or zwitterionic surfactant, which can be included in an amount ranging from 0 to about 8, preferably from 1 to 4 wt %.

Examples of amphoteric and zwitterionic surfactants include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred example is a nonionic surfactant, which can be included in an amount ranging from 0 to 8, preferably from 2 to 5 percent by weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Other representative nonionic surfactants include mono- or di-alkyl alkanolamides. Examples include coco mono- or di-ethanolamide and coco mono-isopropanolamide.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

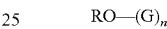

wherein R is a branched or straight chain alkyl group which may be saturated or unsaturated and G is a saccharide group. R may represent a mean alkyl chain length of from about $C_5$ to about $C_{20}$. Preferably R represents a mean alkyl chain length of from about $C_8$ to about $C_{12}$. Most preferably the value of R lies between about 9.5 and about 10.5. G may be selected from $C_5$ or $C_6$ monosaccharide residues, and is preferably a glucoside. G may be selected from the group comprising glucose, xylose, lactose, fructose, mannose and derivatives thereof. Preferably G is glucose.

The degree of polymerisation, n, may have a value of from about 1 to about 10 or more. Preferably, the value of n lies in the range of from about 1.1 to about 2. Most preferably the value of n lies in the range of from about 1.3 to about 1.5.

Suitable alkyl polyglycosides for use in the invention are commercially available and include for example those materials identified as: Oramix NS10 ex Seppic; Plantaren 1200 and Plantaren 2000 ex Henkel.

Other sugar-derived nonionic surfactants which can be included in shampoo compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N—(3-methoxypropyl)glucamide.

A preferred blend of cleansing surfactants is a combination of ammonium lauryl ether sulphate, ammonium lauryl sulphate, PEG 5 cocamide and cocamide MEA (CTFA designations).

The shampoo composition can also optionally include one or more cationic co-surfactants included in an amount ranging from 0.01 to 10, more preferably from 0.05 to 5, most preferably from 0.05 to 2 percent by weight of the composition. Useful cationic surfactants are described hereinbelow in relation to conditioner compositions.

The total amount of surfactant (including any co-surfactant, and/or any emulsifier) in shampoo compositions of the invention is generally from 5 to 50, preferably from 5 to 30, more preferably from 10 to 25 percent by weight of the composition.

Cationic Polymer

A cationic polymer is a preferred ingredient in shampoo compositions according to the invention, for enhancing conditioning performance of the shampoo.

The cationic polymer may be a homopolymer or be formed from two or more types of monomers. The molecular weight of the polymer will generally be between 5 000 and 10 000 000, typically at least 10 000 and preferably in the range 100 000 to about 2 000 000. The polymers will have cationic nitrogen containing groups such as quaternary ammonium or protonated amino groups, or a mixture thereof.

The cationic nitrogen-containing group will generally be present as a substituent on a fraction of the total monomer units of the cationic polymer. Thus when the polymer is not a homopolymer it can contain spacer non-cationic monomer units. Such polymers are described in the CTFA Cosmetic Ingredient Directory, 3rd edition. The ratio of the cationic to non-cationic monomer units is selected to give a polymer having a cationic charge density in the required range.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

The cationic conditioning polymers can comprise mixtures of monomer units derived from amine- and/or quaternary ammonium-substituted monomer and/or compatible spacer monomers.

Suitable cationic conditioning polymers include, for example:

copolymers of 1-vinyl-2-pyrrolidine and 1-vinyl-3-methyl-imidazolium salt (e.g. chloride salt), referred to in the industry by the Cosmetic, Toiletry, and Fragrance Association, (CTFA) as Polyquaternium-16. This material is commercially available from BASF Wyandotte Corp. (Parsippany, N.J., USA) under the LUVIQUAT tradename (e.g. LUVIQUAT FC 370);

copolymers of 1-vinyl-2-pyrrolidine and dimethylaminoethyl methacrylate, referred to in the industry (CTFA) as Polyquaternium-11. This material is available commercially from Gaf Corporation (Wayne, N.J., USA) under the GAFQUAT tradename (e.g., GAFQUAT 755N);

cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquaternium 6 and Polyquaternium 7, respectively;

mineral acid salts of amino-alkyl esters of homo-and co-polymers of unsaturated carboxylic acids having from 3 to 5 carbon atoms, (as described in U.S. Pat. No. 4,009, 256);

cationic polyacrylamides(as described in WO95/22311).

Other cationic conditioning polymers that can be used include cationic polysaccharide polymers, such as cationic cellulose derivatives, cationic starch derivatives, and cationic guar gum derivatives. Suitably, such cationic polysaccharide polymers have a charge density in the range from 0.1 to 4 meq/g.

Cationic polysaccharide polymers suitable for use in compositions of the invention include those of the formula:

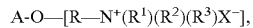

$$A\text{-}O\text{---}[R\text{---}N^+(R^1)(R^2)(R^3)X^-],$$

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Cationic cellulose is available from Amerchol Corp. (Edison, N.J., USA) in their Polymer JR® and LR® series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhone-Poulenc in their JAGUAR trademark series).

Examples are JAGUAR C13S, which has a low degree of substitution of the cationic groups and high viscosity. JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Preferably the cationic conditioning polymer is selected from cationic cellulose and cationic guar derivatives. Particularly preferred cationic polymers are JAGUAR C13S, JAGUAR C15, JAGUAR C17 and JAGUAR C16 and JAGUAR C162.

The cationic conditioning polymer will generally be present in compositions of the invention at levels of from 0.01 to 5, preferably from 0.05 to 1, more preferably from 0.08 to 0.5 percent by weight of the composition.

When cationic conditioning polymer is present in a shampoo composition according to the invention, it is preferred if the copolymer is present as emulsion particles with a mean diameter ($D_{3,2}$ as measured by light scattering using a Malvern particle sizer) of 2 micrometres or less.

Hair Conditioner Compositions

Compositions in accordance with the invention may also be formulated as conditioners for the treatment of hair (typically after shampooing) and subsequent rinsing.

Conditioning Surfactant

Such a conditioner will suitably comprise a conditioning surfactant that is cosmetically acceptable and suitable for topical application to the hair.

Suitable conditioning surfactants are selected from cationic surfactants, used singly or in admixture.

Cationic surfactants useful in compositions of the invention contain amino or quaternary ammonium hydrophilic moieties that are positively charged when dissolved in the aqueous composition of the present invention.

Examples of suitable cationic surfactants are those corresponding to the general formula:

$$[N(R_1)(R_2)(R_3)(R_4)]^+(X)^-$$

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Preferred cationic surfactants for conditioner compositions of the present invention are monoalkyl quaternary ammonium compounds in which the alkyl chain length is C16 to C22.

Other preferred cationic surfactants are so-called dialkyl quaternary ammonium compounds in which R1 and R2 independently have an alkyl chain lengths from C16 to C22 and R3 and R4 have 2 or less carbon atoms.

Examples of suitable cationic surfactants include: cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and salts of these where the chloride is replaced by halogen, (e.g., bromide), acetate, citrate, lactate, glycolate, phosphate nitrate, sulphate, or alkylsulphate. Further suitable cationic surfactants include those materials having the CTFA designations Quaternium-5, Quaternium-31 and Quaternium-18. Mixtures of any of the foregoing materials may also be suitable. A particularly useful cationic surfactant for use in hair conditioners of the invention is cetyltrimethylammonium chloride, available commercially, for example as GENAMIN CTAC, ex Hoechst Celanese.

Salts of primary, secondary, and tertiary fatty amines are also suitable cationic surfactants. The alkyl groups of such amines preferably have from about 12 to about 22 carbon atoms, and can be substituted or unsubstituted.

Particularly useful are amido substituted tertiary fatty amines. Such amines, useful herein, include stearamidopropyidimethylamine, stearamidopropyidiethylamine, stearamidoethyldiethylamine, stearamidoethyldimethylamine, palmitamidopropyld imethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachid amidopropyldiethylamine, arachidamidoethyldiethylamine, arachidamidoethyldimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine. These amines are typically used in combination with an acid to provide the cationic species. The preferred acid useful herein includes L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid. Cationic amine surfactants included among those useful in the present invention are disclosed in U.S. Pat. No. 4,275,055 to Nachtigal, et al., issued Jun. 23, 1981.

The molar ratio of protonatable amines to $H^+$ from the acid is preferably from about 1:0.3 to 1:1.2, and more preferably from about 1:0.5 to about 1:1.1.

In the conditioners of the invention, the level of cationic surfactant is preferably from 0.01 to 10, more preferably 0.05 to 5, most preferably 0.1 to 2 percent by weight of the total composition.

Fatty Materials

Conditioner compositions according to the invention preferably additionally comprise fatty materials. The combined use of fatty materials and cationic surfactants in conditioning compositions is believed to be especially advantageous, because this leads to the formation of a lamellar phase, in which the cationic surfactant is dispersed.

By "fatty material" is meant a fatty alcohol, an alkoxylated fatty alcohol, a fatty acid or a mixture thereof.

Preferably, the alkyl chain of the fatty material is full saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty alcohol material in conditioners of the invention is suitably from 0.01 to 15, preferably from 0.1 to 10, and more preferably from 0.1 to 5 percent by weight of the composition. The weight ratio of cationic surfactant to fatty alcohol is suitably from 10:1 to 1:10, preferably from 4:1 to 1:8, optimally from 1:1 to 1:7, for example 1:3.

Conditioner compositions of the invention can also contain a cationic polymer. Suitable cationic polymers are described hereinabove in relation to shampoo compositions.

Suspending Agents

Hair treatment compositions according to the invention suitably comprise from 0.1 to 5 wt % of a suspending agent. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid crosslinked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol® materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Water-insoluble Oily Conditioning Agents

Hair treatment compositions according to the invention, particularly water-based shampoos and hair conditioners, may also contain, in addition to the copolymer of the invention, one or more further conditioning agents selected from silicone conditioning agents and non-silicone oily conditioning agents.

When conditioning agent is present in the hair treatment compositions in droplet form, the droplets may be liquid, semi-solid or solid in nature, so long as they are substantially uniformly dispersed in the fully formulated product. Any droplets of oily conditioning agent are preferably present as either liquid or semi-solid droplets, more preferably as liquid droplets.

Silicone Conditioning Agents

Aqueous or water-based hair treatment compositions according to the invention can contain conventional silicone conditioning agent in addition to the copolymer of the invention for further enhancing conditioning performance.

Suitable silicones include polydiorganosiloxanes, in particular polydimethylsiloxanes which have the CTFA designation dimethicone. Also suitable for use compositions of the invention particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188. These materials can impart body, volume and stylability to hair, as well as good wet and dry conditioning. Also suitable are functionalised silicones, particularly aminofunctionalised silicones.

Silicone conditioning agents may be added as a separate ingredient into compositions according to the invention. However, it is preferred if any silicones are pre-blended with the copolymer of the invention such that droplets comprising both copolymer and conditioning silicone within the same droplet are present in the composition.

In hair treatment compositions according to the invention, the total amount of silicone material additional to the copolymer according to the invention is suitably in the range from 0.1 to 5%, preferably from 0.3 to 3%, more preferably from 0.5 to 2% by weight of composition.

Non-Silicone Oily Conditioning Components

Compositions according to the present invention may also comprise a dispersed, non-volatile, water-insoluble non-silicone oily conditioning agent.

The oily conditioning agent may suitably be selected from oily or fatty materials, and mixtures thereof.

Suitable oily or fatty materials are selected from hydrocarbon oils, fatty esters and mixtures thereof.

The oily or fatty material is suitably present in shampoo or conditioner compositions at a level of from 0.05 to 10, preferably from 0.2 to 5, more preferably from about 0.5 to 3 percent by weight of the composition.

Mousses

Hair treatment compositions in accordance with the invention may also take the form of aerosol foams (mousses) in which case a propellant must be included in the composition. This agent is responsible for expelling the other materials from the container and forming the hair mousse character.

The propellant gas can be any liquefiable gas conventionally used for aerosol containers. Examples of suitable propellants include dimethyl ether, propane, n-butane and isobutane, used singly or in admixture.

The amount of the propellant gases is governed by normal factors well known in the aerosol art. For hair mousses, the level of propellant is generally from 3 to 30, preferably from 5 to 15 percent by weight of the total composition.

Small quantities of surfactant ranging anywhere from 0.1 to 10, preferably from 0.1 to about 1 percent by weight, for example 0.3 percent by weight, may be present in the hair mousse compositions of the invention. The surfactant may be an anionic, nonionic or cationic emulsifier. Particularly preferred are nonionic emulsifiers which are formed from alkoxylation of hydrophobes such as fatty alcohols, fatty acids and phenols.

Hair Oils and Lotions

Hair oils are also suitable conditioning compositions according to the invention. Hair oils are predominantly comprise water-insoluble oily conditioning materials. Lotions are aqueous emulsions comprising water-insoluble oily conditioning materials. Suitable surfactants can also be included in lotions to improve their stability to phase separation.

Mode of Use

Hair treatment compositions of the invention are primarily intended for topical application to the hair and/or scalp of a human subject, either in rinse-off or leave-on compositions, to improve hair fibre surface properties such as smoothness, softness, manageability, cuticle integrity, and shine.

The invention will be illustrated by the following example:

EXAMPLES

Preparation of the Compound According to Formula Y:

In a round bottomed flask fitted with a condenser, a mechanical stirrer and a dropping funnel, was added hydroxyethoxypropyl terminated polydimethylsiloxane (250 g), triethylamine (6.5 g) and dichloromethane (125 mL). The ingredients were mixed and stirred, followed by dropwise addition of 4-pentenoyl chloride. After addition was completed, the mixture was stirred at room temperature for 2 hrs. Dichloromethane was removed by distillation, and hexane (600 mL) was added. The solid was filtered off, and solution was transferred to top of a silica gel column and further eluted with hexane. The eluent was collected and solvent was evaporated, affording product as a clear liquid.

Preparation of Silicone Comb Polymer by Hydrosilylation:

In a round bottomed flask fitted with a condenser, mechanical stirrer and a dropping funnel, poly(methylhydrosilane)-dimethylsiloxane copolymer (25.0 g) and PDMS graft side chains (129.6 g) were dissolved in toluene (150 mL), and Platinum catalyst (0.26 mL) was added. The reaction mixture was stirred and heated at 50 C for 2 hrs, then cooled to room temperature. Solvent was removed under reduced pressure, and polymer was dried under vacuum at 50 C for 3 hrs.

The Platinum catalyst was Platinum(0)-1,3-divinyl-1,1,3,3-tetramethyldisiloxane complex 3 wt. % solution in xylenes: Chemical formula: $O[Si(CH3)2CH=CH2]2Pt$ (ex. Aldrich).

The poly(methylhydrosilane)-dimethylsiloxane copolymer was from Gelest with a molecular weight of 62,000 and with a molar percentage of 5 to 7 MeHSiO.

The copolymer segments thus made had an average of 51-[SiHCH$_3$O]— monomeric precursor units and 794-[Si(CH$_3$)$_2$O]— monomeric units prior to hydrosilylation with CH$_2$=CH (CH2)$_2$ COO—P where P is a polydimethylsiloxane segment with 69-[Si(CH$_3$)$_2$O]— units. All the end groups for the copolymer segments are based on trimethylsiloxane. In other words, the group L$_1$ of monomer B is CH$_2$CH$_2$CH$_2$CH$_2$COO. From the measured molecular weight of the polymer, the degree of crosslinking was found to be 10, meaning that the polymer molecules had an average of 10 copolymer segments per molecule.

Copolymer Emulsion 1
Copolymer 15%
Laureth-4 (Brij 30 ex ICI) 3%
Laureth-23 (Brij 35 ex ICI) 3%
Cetyl dimethicone copolymer (Abil EM90 ex Goldschidt) 1%
Water to 100%.

A pre-blend of the copolymer and cetyl dimethicone was emulsified into a pre-blended water and surfactant mixture.

A further emulsion of the copolymer was prepared using the following ingredients:

Copolymer Emulsion 2
Copolymer 50%
C$_{12}$-C$_{15}$ ethoxylated primary alcohol (Tergitol TMN 6 ex Union Carbide) 5%
Water to 100%

Hair conditioner compositions were prepared according to the formulations of Examples 1 to 5 shown below in tables 1 and 2.

TABLE 1

| Ingredient | Chemical Name | Example 1 % active | Example A % active | Example B % active | Supplier |
|---|---|---|---|---|---|
| Genamin KDMP | Behenyl Trimethyl Ammonium Chloride | 1.88 | 1.88 | 1.88 | Clariant |
| Laurex CS | Cetearyl Alcohol | 3.76 | 3.76 | 3.76 | Albright & Wilson |
| Nipagin M | Methyl Paraben | 0.19 | 0.19 | 0.19 | Nipa Laboratories |
| Copolymer emulsion 1 | | 3 | 0 | 0 | |
| DC 1785 emulsion | dimethiconol | 0 | 3 | 0 | Dow Corning |
| water | | To 100% | To 100% | To 100% | |

TABLE 2

| Ingredient | Chemical Name | Example 2 % active | Example C % active | Supplier |
|---|---|---|---|---|
| Arquad 16-29 | Cetrimmonium Chloride | 1.58 | 1.58 | Akzo Nobel |
| Arquad 2HT-75% | di(hydrogenated tallow) dimethylammonium chloride | 0.71 | 0.71 | Akzo Nobel |
| Laurex CS | Cetearyl Alcohol | 5.64 | 5.64 | Albright & Wilson |
| Nipagin M | Methyl Paraben | 0.19 | 0.19 | Nipa Laboratories |
| Copolymer emulsion 2 | | 3 | 0 | |
| DC 1785 emulsion | dimethiconol | 0 | 3 | Dow Corning |
| water | | To 100% | To 100% | |

Examples A, B and C are comparative examples whereas examples 1 and 2 are compositions comprising a copolymer according to the invention.

DC 1785, used in the comparative examples is a commercially available silicone used for hair conditioning.

The conditioner compositions were applied to shampooed hair samples followed by rinsing in clean water. The reduction in friction was measured compared to the untreated hair using a laboratory technique with a commercially available texture analyser TA XT2i ex Stable Microsystems. Results are shown in table 3.

TABLE 3

| Example Formulation | % Reduction in friction |
|---|---|
| 1 | 57 |
| 2 | 45 |
| A | 25 |
| B | 15 |
| C | 16 |

Table 4 shows the reduction in friction for hair switches to which copolymers according to the invention were evenly applied in toluene solution such that the dosage of the polymer on the hair was 0.001 g of polymer per gram of hair. All the polymers were made following a process similar to that described above, and had the same organic group L$_3$, i.e. CH$_2$CH$_2$COO, such that the group L$_1$ of monomer B is CH$_2$CH$_2$CH$_2$CH$_2$COO.

The toluene solvent was allowed to evaporate prior to measurement of the friction. As a control, a linear polydimethylsiloxane (DC200, with a viscosity of 60,000 cS (mm$^2$sec$^{-1}$) at 25° C. was applied to a hair switch, under similar conditions. This is marked as comparative example D in the table.

From the results in table 4, it can be seen that the polymers according to the invention, when deposited on the hair, give friction reduction comparable to that of the known polydimethylsiloxane polymer D.

TABLE 4

| Copolymer | p | q | r | mean number of copolymer segments | % Friction Reduction |
|---|---|---|---|---|---|
| 1 | 794 | 51 | 69 | 10 | 52.1 |
| 2 | 18 | 8 | 13 | 14 | 47.0 |
| 3 | 0 | 61 | 138 | 15 | 46.0 |
| 4 | 794 | 51 | 138 | 12 | 45.2 |
| 5 | 18 | 8 | 138 | 14 | 44.8 |
| 6 | 0 | 30 | 138 | 18 | 44.0 |
| 7 | 168 | 5 | 13 | 2 | 43.9 |
| 8 | 168 | 5 | 138 | 4 | 42.0 |
| 9 | 0 | 61 | 13 | 23 | |
| 10 | 0 | 30 | 69 | 19 | 41.8 |
| 11 | 18 | 8 | 69 | 15 | 39.9 |
| 12 | 0 | 30 | 13 | 16 | 37.7 |
| D | — | — | — | — | 44.9 |

The invention claimed is:

1. A composition for personal, home, or laundry treatment comprising a polymer which comprises:
  (a) copolymer segment, the copolymer segment having a silicone backbone which is furnished with silicone substituent groups in order to form a comb or rake shaped molecule, comprising monomeric units according to formula A:

$$-[SiR_1R_2-O]-, \quad A)$$

and monomeric units according to formula B:

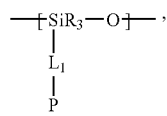

and
  (b) end groups,
  wherein $L_1$ is an organic linking group and P is a polymer comprising 2 or more monomeric units G;

$$-[SiR_4R_5-O]- \quad G)$$

and P further comprises an end group,
  wherein $R_1$, $R_2$, $R_3$, $R_4$ and $R_5$ are independently selected from the group consisting of
  hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, and combinations thereof, wherein the copolymer segment comprises by number an average of p monomeric units according to formula A and q monomeric units according to formula B and wherein B comprises an average of monomeric units according to formula G, wherein p is from 40 to 15000, q is from 5 to 500 and r is from 10 to 500.

2. A composition as claimed in claim 1 further comprising 40% or more by weight of water.

3. A composition as claimed in claim 1 wherein the copolymer is present as the oil phase of an oil-in-water emulsion.

4. A composition according to claim 1 wherein $R_1$, $R_2$, $R_3$, $R_4$ and $R_5$ each independently have from 1 to 40 carbon atoms.

5. A composition according to claim 1 wherein $R_1$, $R_2$, $R_3$, $R_4$ and $R_5$ are methyl groups.

6. A composition according to claim 1 wherein the end groups are selected from —Si(CH$_3$)$_3$, Si(CH$_3$)$_2$OH, —O—Si (CH$_3$)$_3$, —O—Si(CH$_3$)$_2$OH and mixtures thereof.

7. A composition according to claim 1 wherein the linking group -$L_1$- comprises the grouping —CH$_2$—(CH$_2$)$_n$-$L_2$- wherein n is from 1 to 8, and $L_2$ is a linking group which is absent or selected from the group consisting of ether, amido and ester linkages.

8. A composition for personal, home, or laundry treatment comprising a polymer which comprises:
  (a) a copolymer segment, the copolymer segment having a silicone backbone which is furnished with silicone substituent groups in order to form a comb or rake shaped molecule, comprising monomeric units according to formula A:

$$-[SiR_1R_2-O]-, \quad A)$$

and monomeric units according to formula B:

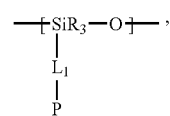

and
  (C) monomeric units which are amino-functionalised organosiloxane units; and
  (b) end groups,
  wherein $L_1$ is an organic linking group and P is a polymer comprising 2 or more monomeric units G;

$$-[SiR_4R_5-O]- \quad G)$$

and P further comprises an end group,
  wherein $R_1$, $R_2$, $R_3$, $R_4$ and $R_5$ are independently selected from the group consisting of
  hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, and combinations thereof.

9. A composition according to claim 1 wherein the polymer consists essentially of a single copolymer segment and end groups.

10. A composition for personal, home, or laundry treatment comprising a polymer which comprises:
  (a) a copolymer segment, the copolymer segment having a silicone backbone which is furnished with silicone substituent groups in order to form a comb or rake shaped molecule, comprising monomeric units according to formula A:

$$-[SiR_1R_2-O]-, \quad A)$$

and monomeric units according to formula B:

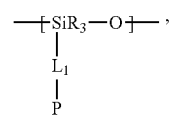

and
(b) end groups,
wherein $L_1$ is an organic linking group and P is a polymer comprising 2 or more monomeric units G;

$$—[SiR_4R_5—O]—$$

and P further comprises an end group,
wherein $R_1$, $R_2$, $R_3$, $R_4$ and $R_5$ are independently selected from the group consisting of
hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, and combinations thereof; wherein the polymer comprises 2 or more copolymer segments crosslinked by a crosslinking unit.

11. A composition according to claim 10 wherein the crosslinking unit comprises a polyorganosiloxane segment.

12. A composition according to claim 1 wherein 90% or more by weight of the polymer is comprised of the monomeric units A, B and G of claim 1.

13. A composition according to claim 1 wherein the copolymer is obtained by a process comprising the steps of:
   i) forming a copolymer backbone precursor comprising monomeric units according to formula A:

$$—[SiR_1R_2—O]— \qquad A)$$

and
monomeric precursor units according to formula X:

$$—[SiHR_3—O]— \qquad X)$$

ii) reacting the copolymer backbone precursor with a compound according to formula Y;

$$CH_2{=}CH\text{-}L_3\text{-}P \qquad Y)$$

in a hydrosilylation reaction in the presence of a suitable catalyst,
wherein $L_3$ is an organic group which may be absent and wherein the quantity of Y is such that the monomeric precursor units X are substantially converted to the monomeric units B of the copolymer segment of claim 1.

14. A composition according to claim 13 wherein the hydrosilylation reaction is carried out with a crosslin king agent present at 0.01 to 20% by weight of the compound according to formula Y whereby the resulting copolymer is crosslinked.

15. A composition according to claim 1 which is a hair treatment composition.

16. A composition according to claim 10 wherein the polymer consists essentially of 2 or more crosslinked copolymer segments comprising by number an average of p monomeric units according to formula A, q monomeric units according to formula B and wherein P comprises an average of r monomeric units G, wherein p is from 700 to 900, q is from 40 to 60 and r is from 60 to 75, wherein $R_1$, $R_2$, $R_3$, $R_4$ and $R_5$ are methyl groups, and wherein $L_1$ is $(CH_2)_4COO$.

17. A method of treating hair by applying to the hair a composition according to claim 15.

* * * * *